United States Patent
Friesz

(10) Patent No.: US 9,174,958 B2
(45) Date of Patent: Nov. 3, 2015

(54) PROCESS FOR THE PREPARATION OF DRONEDARONE

(71) Applicant: SANOFI, Paris (FR)

(72) Inventor: Antal Friesz, Budapest (HU)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/711,891

(22) Filed: Dec. 12, 2012

(65) Prior Publication Data

US 2013/0109868 A1    May 2, 2013

Related U.S. Application Data

(63) Continuation of application No. PCT/HU2011/000054, filed on Jun. 10, 2011.

(30) Foreign Application Priority Data

Jun. 18, 2010  (HU) ................................ 1000330

(51) Int. Cl.
C07D 307/80    (2006.01)

(52) U.S. Cl.
CPC .................................. C07D 307/80 (2013.01)

(58) Field of Classification Search
CPC .................................................... C07D 307/80
USPC ........................................................ 549/468
See application file for complete search history.

(56) References Cited

U.S. PATENT DOCUMENTS

| | | | |
|---|---|---|---|
| 3,577,441 A | 5/1971 | Kaminsky et al. |
| 3,657,350 A | 4/1972 | Mooradian et al. |
| 3,937,737 A | 2/1976 | Eiglmeier |
| 4,243,405 A | 1/1981 | Balasubramanyan et al. |
| 4,666,931 A | 5/1987 | Ohishi et al. |
| 5,066,803 A | 11/1991 | D'Ambra et al. |
| 5,223,510 A | 6/1993 | Gubin et al. |
| 6,555,697 B1 | 4/2003 | Schlama |
| 6,828,448 B2 | 12/2004 | Fino et al. |
| 6,846,936 B2 | 1/2005 | Biard |
| 6,855,842 B1 | 2/2005 | Schlama et al. |
| 6,949,583 B2 | 9/2005 | Assens et al. |
| 6,984,741 B2 | 1/2006 | Magerlein |
| 7,148,240 B2 | 12/2006 | Assens et al. |
| 7,312,345 B2 | 12/2007 | Gutman et al. |
| 7,517,876 B2 | 4/2009 | Klein et al. |
| 8,143,269 B2 | 3/2012 | Whitten et al. |
| 8,501,971 B2 | 8/2013 | Friesz et al. |
| 8,658,808 B2 | 2/2014 | Kretzschmar et al. |
| 8,658,809 B2 | 2/2014 | Friesz et al. |
| 8,674,121 B2 | 3/2014 | Kretzschmar et al. |
| 8,686,180 B2 | 4/2014 | Bon et al. |
| 8,748,636 B2 | 6/2014 | Bailly et al. |
| 8,796,489 B2 | 8/2014 | Bailly et al. |
| 8,816,103 B2 | 8/2014 | Friesz et al. |
| 8,871,956 B2 | 10/2014 | Bailly et al. |
| 8,884,033 B2 | 11/2014 | Bon et al. |
| 8,889,734 B2 | 11/2014 | Friesz et al. |
| 8,962,869 B2 | 2/2015 | Grimaud et al. |
| 9,024,046 B2 | 5/2015 | Friesz et al. |
| 2004/0010032 A1 | 1/2004 | Biard |
| 2004/0048921 A1 | 3/2004 | Fino et al. |
| 2008/0033209 A1 | 2/2008 | Szarvas et al. |
| 2010/0087415 A1 | 4/2010 | Whitten et al. |
| 2010/0273764 A1 | 10/2010 | Andrews et al. |
| 2012/0065411 A1 | 3/2012 | Kretzschmar et al. |
| 2012/0077995 A1 | 3/2012 | Kretzschmar et al. |

(Continued)

FOREIGN PATENT DOCUMENTS

| CN | 101838252 A | 9/2010 |
|---|---|---|
| CN | 101993427 A | 3/2011 |

(Continued)

OTHER PUBLICATIONS

Groves, J.K. Chem. Soc. Rev. 1972, 1, 73-97.
U.S. Appl. No. 13/599,374, filed Aug. 30, 2012, Bailly, et al.
U.S. Appl. No. 13/638,484, filed Aug. 30, 2012, Bailly, et al.
U.S. Appl. No. 13/638,500, filed Sep. 28, 2012, Priem, et al.
U.S. Appl. No. 13/628,867, filed Sep. 27, 2012, Bon, et al.
International Search Report for WO2011/158050 dated Dec. 22, 2011.
Abramenko et al. (1975). "Polymethine Dyes—Furo[2,3-g] Benzothiazole Derivatives," Chemistry of Heterocyclic Compounds 11:1361-1364.

(Continued)

*Primary Examiner* — Andrew D Kosar
*Assistant Examiner* — Laura Daniel
(74) *Attorney, Agent, or Firm* — Morrison & Foerster LLP

(57) ABSTRACT

This disclosure relates to a process for the preparation of N-[2-n-butyl-3-{4-[(3-dibutylamino)-propoxy]-benzoyl}-1-benzofuran-5-yl]-methane-sulfonamide of formula I

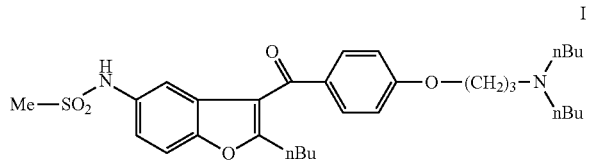

and its pharmaceutically acceptable salts, wherein one of the methylsulfonyl groups of the 2-n-butyl-3-[(di-n-butylamino-3-propoxy)-benzoyl]-5-bis-(methylsulfonamido)-benzofuran of formula II

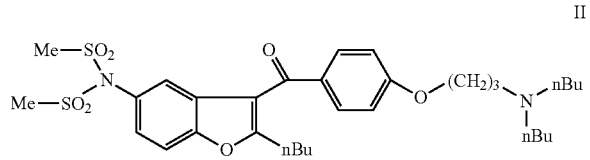

is selectively cleaved and if desired, the resulting compound of formula I is transformed into its salt.

17 Claims, No Drawings

(56) References Cited

U.S. PATENT DOCUMENTS

| | | |
|---|---|---|
| 2012/0289717 A1 | 11/2012 | Friesz et al. |
| 2012/0330036 A1 | 12/2012 | Friesz et al. |
| 2013/0023678 A1 | 1/2013 | Priem et al. |
| 2014/0018553 A1 | 1/2014 | Grimaud et al. |
| 2014/0081035 A1 | 3/2014 | Friesz et al. |
| 2014/0114081 A1 | 4/2014 | Friesz et al. |
| 2015/0005515 A1 | 1/2015 | Friesz et al. |
| 2015/0018568 A1 | 1/2015 | Friesz |
| 2015/0031901 A1 | 1/2015 | Bon et al. |
| 2015/0031902 A1 | 1/2015 | Huszar et al. |

FOREIGN PATENT DOCUMENTS

| | | | |
|---|---|---|---|
| EP | 0471609 | 2/1992 | |
| EP | 0 735 083 A1 | 10/1996 | |
| FR | 2 833 259 A1 | 6/2003 | |
| WO | WO-96/05190 A1 | 2/1996 | |
| WO | WO-02/48078 A1 | 6/2002 | |
| WO | WO 02/48132 | 6/2002 | |
| WO | WO 03/040120 | 5/2003 | |
| WO | WO-2005/012301 A1 | 2/2005 | |
| WO | WO-2007/022501 A2 | 2/2007 | |
| WO | WO-2007/022501 A3 | 2/2007 | |
| WO | WO-2007/100295 A1 | 9/2007 | |
| WO | WO-2007/133637 A2 | 11/2007 | |
| WO | WO-2007/133637 A3 | 11/2007 | |
| WO | WO-2007/140989 A2 | 12/2007 | |
| WO | WO-2007/140989 A3 | 12/2007 | |
| WO | WO-2009/044143 A2 | 4/2009 | |
| WO | WO-2009/044143 A3 | 4/2009 | |
| WO | WO-2010/038029 A1 | 4/2010 | |
| WO | WO-2010/040261 A1 | 4/2010 | |
| WO | WO-2010/116140 A1 | 10/2010 | |
| WO | WO-2010/136500 A1 | 12/2010 | |
| WO | WO-2010/136502 A1 | 12/2010 | |
| WO | WO-2011/070380 A1 | 6/2011 | |
| WO | WO 2011099010 A1 * | 8/2011 | ............ A01N 43/08 |
| WO | WO-2011/104591 A1 | 9/2011 | |
| WO | WO-2011/107705 A1 | 9/2011 | |
| WO | WO-2011/158050 A1 | 12/2011 | |
| WO | WO-2012/004658 A2 | 1/2012 | |
| WO | WO-2012/004658 A3 | 1/2012 | |
| WO | WO 2012/010788 | 1/2012 | |
| WO | WO 2012/010802 | 1/2012 | |
| WO | WO 2012/010913 | 1/2012 | |
| WO | WO-2012/032545 A1 | 3/2012 | |
| WO | WO 2012/127173 | 9/2012 | |
| WO | WO 2012/131408 | 10/2012 | |
| WO | WO 2012/131409 | 10/2012 | |
| WO | WO 2012/131410 | 10/2012 | |
| WO | WO-2013/014478 A1 | 1/2013 | |
| WO | WO-2013/014479 A1 | 1/2013 | |
| WO | WO-2013/014480 A1 | 1/2013 | |
| WO | WO-03/048144 A2 | 6/2013 | |
| WO | WO-03/048144 A3 | 6/2013 | |
| WO | WO-2013/121234 A1 | 8/2013 | |
| WO | WO-2013/121235 A2 | 8/2013 | |
| WO | WO-2013/121235 A3 | 8/2013 | |
| WO | WO-2013/128294 A2 | 9/2013 | |
| WO | WO-2013/128294 A3 | 9/2013 | |
| WO | WO-2013/128294 A8 | 9/2013 | |

OTHER PUBLICATIONS

Adams et al. (1951). Quinone imides. IV. P-Quinone monosulfonimides. Journal of the American Chemical Society 73:1145-1149.

Adams et al. (1956). "Quinone Imides. XXXIX. Adducts of Quinone Monoimides and Conversion of Active Methylene Adducts to Benzofurans," *J. Am. Chem. Soc.* 78(3):658-663.

Alcaraz et al. (2004). "Novel N-Aryl and N-Heteroaryl Sulfamide Synthesis via Palladium Cross Coupling," Organic Letters 6(16):2705-2708.

Ando et al. (1982). "Motion at the Active Site of Tosylchymotrypsin," *Journal of the American Chemical Society* 104(11):3172-3178.

Anjanappa et al. (2008). "2-(Trimethylsilyl)ethanesulfonyl amide as a new ammonia equivalent for palladium-catalyzed amination of aryl halides," Tetrahedron Letters 49:4585-4587.

Bartoli et al. (1991). "Unexpected Elimination to α,β-Alkynylketones in the Reaction of Dianions of 1-Arylenaminones with Trimethylchlorosilane," Tetrahedron Letters 32(48):7091-7092.

Batra et al. (2001). "Syntheses and Biological Evaluation of Alkanediamines as Antioxidant and Hypolipidemic Agents," Bioorganic & Medicinal Chemistry 9(12):3093-3099.

Bavin (1973). "2-Aminofluorene," *Org. Syn. Coll.* 5:30.

Berthold et al. (2002). "Transfer Hydrogenation in Ionic Liquids under Microwave Irradiation," *Syn.* 1607-1610.

Boovanahalli et al. (2004). "Application of Ionic Liquid Halide Nucleophilicity for the Cleavage of Ethers: A Green Protocol for the Regeneration of Phenols from Ethers," Journal of Organic Chemistry 69:3340-3344.

Bourgery et al. (1981). "Synthesis and Antiarrhythmic Activity of New Benzofuran Derivatives," Journal of Medicinal Chemistry 24(2):159-167.

Burton et al. (2003). "Palladium-Catalyzed Intermolecular Coupling of Aryl Chlorides and Sulfonamides under Microwave Irradiation," Organic Letters 5(23):4373-4376.

Castellino et al. (1984). "Synthesis of Benzofurans from Oxygenated Phenoxyamines," Journal of Organic Chemistry 49:4399-4404.

Chauhan et al. (2004). "Microwave assisted dealkylation of alkyl aryl ethers in ionic liquids," Journal of Chemical Research, pp. 693-694.

Cheng et al. (2007). "Facile Cleavage of Ethers in Ionic Liquid," Bulletin of the Chemical Society of Japan 80(10):2008-2010.

Database PubChem Compound [Online] (Oct. 25, 2006),"CID 10095002—Compound Summary:N-[3-[4-(3-aminopropoxy)benzoyl]-2-butyl-1-benzofuran-5-yl", XP002676507, Database accession No. 15082344. Retrieved from the Internet: URL:http://pubchem.ncbi.nlm.nih.gov/summary/summary.cgi?sid=15082344&viewopt=PubChem [retrieved on May 23, 2012].

Delahay et al. (2007). "Past and Recent Approaches of Preparing Fe-ZSM-5," *Current Topics in Catalysis* 6:19-33.

Douglass (1959). "Some New Reactions of Methanesulfenyl Chloride," *Journal of Organic Chemistry* 24:2004-2006.

Denmark et al. (2008). "Lewis base catalysis in organic synthesis," *Angew. Chem. Int. Ed.* 47(9):1560-1638.

Fennel (1958). "Quinoline Analogs of Podophyllotoxin. I. Preliminary Experiments. Syntheses of Some 4-Phenylquinoline Derivatives," J. Org. Chem. 23:432-434.

Fieser et al. (1967). "Reagents for Organic Synthesis," John Wiley & Sons, pp. 703-705.

Fontana (2008). "Syntheses of (R,S)-Naproxen and its 6-O-Desmethyiated metabolite labelled with 2H," *J. Labelled Compounds and Radiopharma.* 51:239-241.

Gilow et al. (Jun.-Jul. 1991). "Sulfenylation of Some Pyrroles and Indoles," *J. Het. Chem.* 28:1025-1034.

Gutowski et al, (2005). "Prediction of the Formation and Stabilities of Energetic Salts and Ionic Liquids Based on ab Initio Electronic Structure Calculations," The Journal of Physical Chemistry B 109:23196-23208.

Haddadin et al. (1976). "Reaction to Benzofurazan Oxide with Unsymmetrical 1, 3-Diketones: Steric Polar Effects," *Tetrahedron* 32:719-724.

Hauser et al. (1948) "Alkaline cleavage of unsymmetrical β-diketones. Ring opening of acylcyclohexanones to form ϵ-acylcaproic acids," Journal of the American Chemical Society. 70:4023-4026.

Headley et al. (2006). "Dynamic Solvation in Imidazolium-Based Ionic Liquids on Short Time Scales," Journal of Physical Chemistry 110:9549-9554.

Horton et al. (1967). "Reactions With Reactive Alkyl Halides," *J. Meth. In Enzymology* 11:556-565.

Ikawa et al. (2007). "Pd-Catalyzed Amidations of Aryl Chlorides Using Monodentate Biaryl Phosphine Ligands: A Kinetic, Computational, and Synthetic Investigation," Journal of the American Chemical Society 129:13001-13007.

(56) References Cited

OTHER PUBLICATIONS

Imori et al. (2006). "Efficient Demethylation of N, N-Dimethylanilines with Phenyl Chloroformate in Ionic Liquids," *Synlett*. 16:2629-2632.
Johnson Matthey Handbook of Pharmaceutical Catalysis, 2009, pp. 1-106.
Joshi et al. (1986). "Some New Fluorinated β-Ketoamines and Their Copper Complexes," Synth. React. Inorg. Met. -Org. Chem. 16(7):1009-1024.
Krongauz et al. (1986). Poly(anilophenylquinoxaline)s. Inst. Elementoorg. Soedin. 28(4):771 (Abstract).
Kurti et al. (2005). Strategic Applications of Named Reactions in Organic Synthesis. El Sevior, pp. 448-449.
Kwiatkowski et al. (1978). "Metal Benzoylpivaloylmethanates, Part I. Free Ligands and Copper(II) Chelates," Transition Met. Chem. 3:305-308.
Laszlo et al. (1987). "Catalysis of Friedel-Crafts Alkylation by a Montmorillonite Doped with Transition-Metal Cations," Helvetica Chimica Acta 70:577-586.
Liu et al. (2004). "Cleavage of Methyl Ethers of Flavones by Chloroaluminate Ionic Liquid," Synthetic Communications 34:3209-3218.
Majdik (1985). "Studiul reactiei de ciclizare a orto-hidroxibenzilfenilcetonelor in benzofuran derivati," Revista de Chimie 36(8):760-761 (with English Translation).
Majdik et al. (1989). "Prepararea unor 2-(aril)-nitrobenzofurani din 0-(nitrofenil)-acetofenonoxime," Revista de Chemie, vol. 40, No. 8, pp. 689-693 (with English Translation).
Majdik et al. (1989). "0-Arilarea cetoximelor cu nitroclorbenzeni," Revista de Chemie, vol. 40, No. 6, pp. 490-493 (with English Translation).
March (Jul. 1, 1992). "Aromatic Electrophilic Substitution," Chapter 11 in *Advanced Organic Chemistry, Reactions, Mechanism and Structure*, 4th edition, Wiley Interscience, pp. 538-542.
March (Jul. 1, 1992). "Aliphatic Nucleophilic Substitution," Part 2 in *Advanced Organic Chemistry, Reactions, Mechanism and Structure*, 4th edition, Wiley Interscience, pp. 442.
Marvel et al. (1941). "Diphenylacetic Acid," *Org. Synth. Coll.* vol. 1, 224-225.
Mehrotra et al. (2001). "Search for new chemical entities as menses inducing agents," Contraception. 64:187-191.
Munch et al. (1946). "The Preparation of Some α-Dialkylamino-ω-Methylaminoalkanes," *J. Am. Chem. Soc.* 68:1297-1299.
Nagy et al. (2007). "Isomorphous Substitution in Zeolites," Mol. Sieves 5:365-478.
Nakamura et al. (2004). "Pyrazole Derivatives as new potent and selective 20-hydroxy-5,6,11,14-Eicosatetraenoic Acid Synthase Inhibitors," *Bioorganic Medic. Chem*. 12:6209-6219.
Pal et al. (2007). "Synthesis of monohydroxy-functionalized triphenylene discotics: green chemistry approach," Tetrahedron 63:6874-6878.
Roshchin et al. (1998). "Synthesis of Benzofurans via Pd2+-Catalyzed Oxidative Cyclization of 2-Allylphenols," Journal of Organometallic Chemistry 560(1-2):163-167.
Sanfilippo (1988). "Synthesis of (aryloxy)alkylamines. 1. Novel antisecretory agents with H+K+-ATPase inhibitory activity," *J. Med. Chem*. 31(9):1778-1785.
Serajuddin (2007). "Salt formation to improve drug solubility," Advanced Drug Delivery Reviews 59:603-616.
Shridhar (1981). "Synthesis & Biological Activity of Some New 2-[(5-Nitro-2-furyl- & 5-nitro-2-thienyl)vinyl]-N-arylsulphonamides & 1-[2-(5-Nitro-2-furyl & 5-nitro-2-thienyl)vinyl]sulphonyl Heterocycles," Indian Journal of Chemistry 208:234-237.
Skeels et al. (1989). "Zeolite Chemistry, Substitution of iron or titanium for Aluminum in Zeolites via reaction with the respective ammonium fluoride salts," *ACS Symposium series, zeolite Synthesis* 398:420-435.
Ślusarska et al. (Feb. 1981). "One-Pot Phase-Transfer-Catalysed N-Alkylation of Diphenylphosphinamide with Alcohols in the Presence of Methanesulfonyl Chloride," Synthesis 155-156.
Son et al. (1989). "Stereochemical Mechanism of Iodoacetic Acid Mediated Decomposition of $_L$-Methionine to $_L$-Homoserine Lactone," *Journal of the American Chemical Society* 11 1(4):1363-1367.
Sun et al. (2004). "N-{2-{2-(4-Phenylbutyl)benzofuran-4-yl]cyclopropylmethyl)-acetamide: an orally bioavailable melatonin receptor agonist," Bioorganic & Medicinal Chemistry Letters 14:5157-5160.
Tanaka (1967). Studies on 5-Aminosalicylaldehyde Derivatives. II. Reduction of 5-(p-Sulfophenylazo)salicylaldehyde Through Poly(5-Nitrilosalicylidene) to 5-Aminosalicylaldehyde Derivatives, Bulletin of the Chemical Society of Japan 40(7):1724-1726.
Thornber (1979). "Isosterism and molecular modification in drug design." Chem. Soc. Rev. 8:563-580.
Upthagrove et al. (Nov. 2001). "Importance of Amine $pK_a$ and Distribution Coefficient in the Metabolism of Fluorinated Propranolol Derivatives. Preparation, Identification of Metabolite Regioisomers, and Metabolism by CYP2D6," *Drug Metab. Dispos*. 29(11):1377-1388.
Wamser et al. (1989). "Kinetics and Mechanisms for the Two-phase Reaction between Aqueous Aniline and Benzoyl Chloride in Chloroform, with and without Pyridine Catalysis," J. Org. Chem. 54:150-154.
Weissman et al. (2005). "Recent advances in ether dealkylation," Tetrahedron 61:7833-7863.
Weitkamp et al. (1986). "Isomorphe Substitution in Zeolithen: Katalyse an Boro-, Alumo-und Galio-Silicaten mit ZSM-5-Strukter," *Chem. Ing. Tech*. 58(12):969-971 (with English Translation).
Wikipedia. (Nov. 5, 2012). "Reduction of Nitro Compounds.".
Wu et al. (2004). "Immobilization of HX: [Hmim]X as Halogenating Agent, Recyclable Catalyst and Medium for Conversion of Alcohols to alkyl halides," *Chinese J. Chem*. 22:619-621.
Wuts (2006). Greene's Protective Groups in Organic Synthesis, Fourth Edition, John Wiley and Sons, Chapter 7, Protection for the Amino Group, pp. 696-926.
Yang et al. (2009). "Structure-based virtual screening for identification of novel 11 β-HSD1 inhibitors," European J. of Medicinal Chem. 44(3):1167-1171.
Yin et al. (2000). "Palladium-Catalyzed Intermolecular Coupling of Aryl Halides and Amides," Organic Letters 2(8):1101-1104.
Yin et al. (2002). "Pd-Catalyzed Intermolecular Amidation of Aryl Halides: The Discovery that Xantphos Can Be Trans-Chelating in a Palladium Complex," Journal of the American Chemical Society 124:6043-6048.
Zasshi (1956). "Studies on the Syntheses of Phenothiazine Derivatives. I. Syntheses of N-Substituted Phenothiazines by Tosylates," *J. Pharm. Soc. Of Japan* 76:637-640 (with English Translation).
U.S. Appl. No. 14/377,484, filed on Aug. 7, 2014, by Huszar et al.
U.S. Appl. No. 14/403,528, filed on Nov. 24, 2014, by Huszar et al.

* cited by examiner

PROCESS FOR THE PREPARATION OF DRONEDARONE

This application is a continuation of International Application No. PCT/HU2011/000054, filed Jun. 10, 2011, which is incorporated herein by reference and which claims the benefit of priority of Hungarian Patent Application No. P1000330, filed Jun. 18, 2010.

This invention relates to a novel process for the preparation of N-[2-n-butyl-3-{4-[(3-di-n-butylamino)-propoxy]-benzoyl}-1-benzofuran-5-yl]-methane-sulfonamide (dronedarone) and its pharmaceutically acceptable salts and to the novel intermediates used in this process.

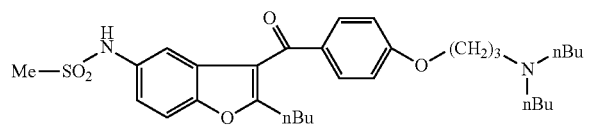

I

Dronedarone of the formula I is useful in the treatment of certain pathological changes of the cardiovascular system, first of all in the treatment of angina pectoris, high blood pressure, arrhythmia and insufficient cerebral blood flow (EP 0471609 B1).

Presently several methods for the preparation of Dronedarone of the formula I are known. In one of the prior art methods (EP 0471609 B1) the 2-n-butyl-5-nitro-benzofuran of formula IX

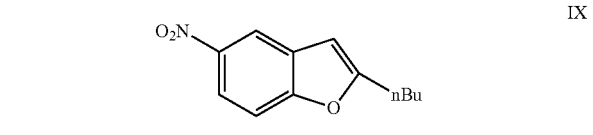

IX is reacted with anisoyl chloride under Friedel-Crafts conditions, and by heating the resulting 2-n-butyl-3-(4-methoxy-benzoyl)-5-nitro-benzofuran of formula X

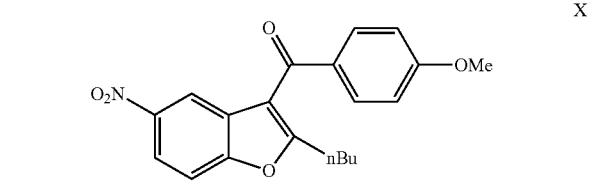

X in the presence of aluminum chloride

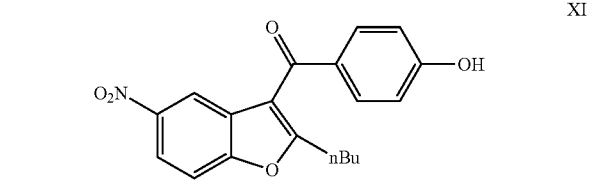

XI the 2-n-butyl-3-(4-hydroxy-benzoyl)-5-nitro-benzofuran of formula XI is obtained.

Utilization of this reaction step in industrial scale, however, involves difficulties, since the compound of formula X is mutagenic, and aluminum chloride is harmful for the health. Reaction of the resulting compound of formula XI with di-n-butylamino-propyl chloride gives the 2-n-butyl-3-[4-(3-di-n-butylamino-propoxy)-benzoyl]-5-nitro-benzofuran of formula XII

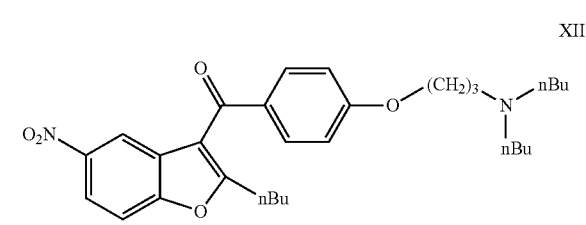

XII which on reduction with platinum oxide catalyst gives the 5-amino-2-n-butyl-3-[4-(3-di-n-butylamino-propoxy)-benzoyl]-benzofuran of formula XIII.

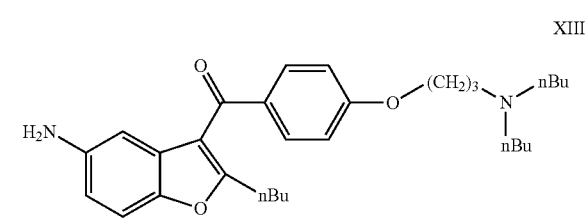

XIII

Finally, mesylation the compound of formula XIII results dronedarone of formula I.

This is a linear synthesis, where the parts of the desired molecule are built up stepwise, using more and more complicated molecules in the consecutive steps, which is economically unfavourable.

In the last step, the selective mesylation of the amino group of the compound of formula XIII is difficult, the double mesylated 2-n-butyl-3-[(di-n-butylamino-3-propoxy)-benzoyl]-5-bis-(methylsulfonamido)-benzofuran derivative of formula II is also formed and it appears beside the dronedarone of formula I.

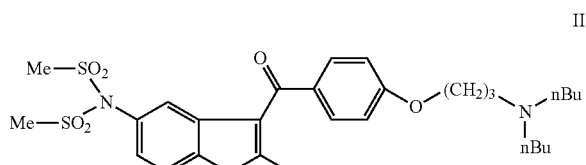

II

According to the literature, this process, after purification by column chromatography, results in 61.6% yield, but the process is complicated, not suitable for industrial application.

Another process for the preparation of dronedarone is described in patent application of publication number WO 02/48132. This super-convergent route consists of the following steps:

The 5-amino-2-n-butyl-benzofuran of formula XIV

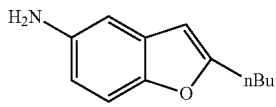

XIV is mesylated and the resulting 2-n-butyl-5-methylsulfonamido-benzofuran of formula XV

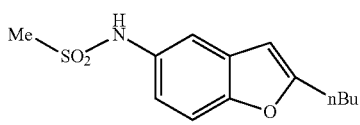

XV is reacted under Friedel-Crafts conditions with the hydrochloride salt of the 4-[3-(di-n-butylamino)propoxy]-benzoyl chloride of formula VIII

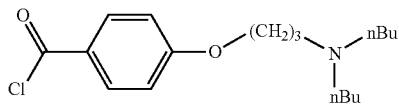

VIII to obtain the hydrochloride salt of dronedarone of formula I.

In this method the sequence of the reaction steps is changed, the reduction and the mesylation steps are at the beginning of the synthesis.

This method is very simple and economical as regards the number of the reaction steps. Its drawback is, however, that in the last step the hydrochloride salt of dronedarone is obtained in a rather contaminated form. This can be explained by the presence of the dibutylamino-propyl group in the Friedel-Crafts reaction. In the examples of WO02/48132 the yield is 90%, during the purification steps at first the raw dronedarone hydrochloride salt, then following treatment with hydrogen chloride solution in isopropanol, the purified dronedarone hydrochloride salt is obtained (90%). It means that the yield of the raw dronedarone hydrochloride is 90% and then the purification step has a yield of 90%. Another drawback of the method is that the reactants used in the Friedel-Crafts reaction and the obtained by-products are insoluble in water, thus they cannot be removed from the system by aqueous washing.

Our aim was to work out a novel method for the preparation of dronedarone and its pharmaceutically acceptable salts, which method avoids the above mentioned disadvantages of known processes and it is economical and industrially applicable.

We have found that if one methylsulfonyl group of the 2-n-butyl-3-[(di-n-butylamino-3-propoxy)-benzoyl]-5-bis-(methylsulfonamido)-benzofuran of formula II

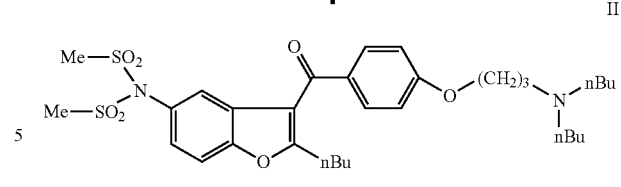

II is selectively cleaved, then dronedarone of formula I is obtained in good yield and in appropriate purity.

According to our invention the cleavage of one of the methylsulfonyl groups of the compound of formula II is performed in an alcoholic solvent or in the mixture of alcoholic solvents, in the presence of an alkali alcoholate. As for alcoholic solvent, methanol, ethanol or the mixture of them can be used. As for alkali alcoholate, sodium methylate, potassium methylate, sodium ethylate or potassium ethylate can be applied.

In one embodiment of the process according to our invention, the 2-n-butyl-5-bis-(methylsulfonamido)-benzofuran of the formula III

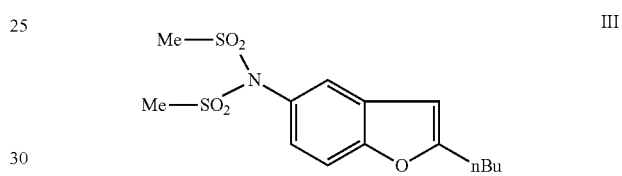

III is reacted under Friedel Crafts conditions with anisoyl chloride, and the resulting 2-n-butyl-5-bis-(methylsulfonamido)-3-(4-methoxy-benzoyl)-benzofuran of formula VII

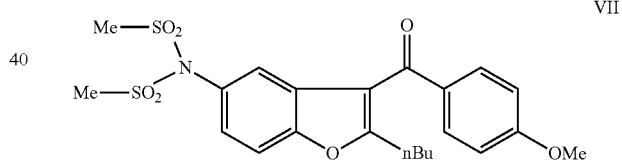

VII is demethylated, and the thus obtained 2-n-butyl-3-(4-hydroxy-benzoyl)-5-bis-(methylsulfonamido)-benzofuran of formula VI

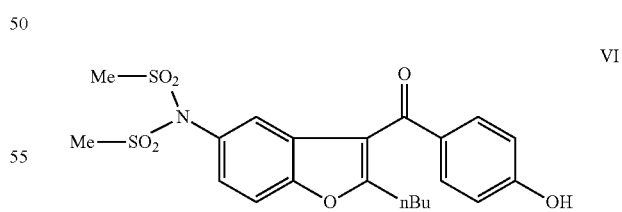

VI is reacted with the 3-di-n-butylamino-propyl chloride of formula V

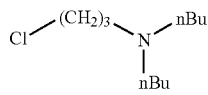

V and from the resulting 2-n-butyl-3-[(di-n-butylamino-3-propoxy)-benzoyl]-5-bis-(methylsulfonamido)-benzofuran of formula II

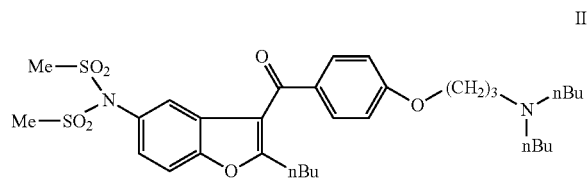

one of the methylsulfonyl groups is selectively cleaved by the method described above.

In another embodiment of the process according to the invention, the 2-n-butyl-5-(bis-methylsulfonamido)-benzofuran of formula III

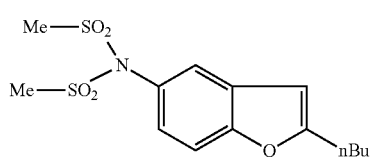

is reacted under Friedel-Crafts conditions with the hydrochloride of the 4-(3-di-n-butylamino-propoxy)-benzoic acid of formula VIII

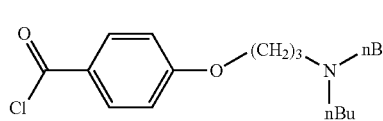

and from the thus obtained 2-n-butyl-3-[(di-n-butylamino-3-propoxy)-benzoyl]-5-bis-(methylsulfonamido)-benzofuran of formula II

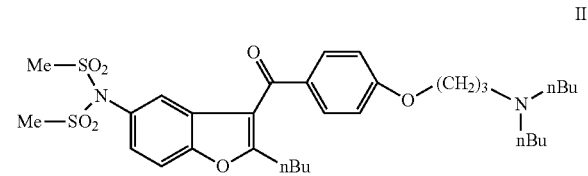

one of the methylsulfonyl groups is selectively cleaved by the method described above.

According to our invention the reaction of the compound of formula III with anisoyl chloride is carried out in an inert organic solvent or in the mixture of inert organic solvents. As for inert organic solvent, halogenated organic solvents (dichloromethane, dichloroethane, chlorobenzene) are applied.

The reaction of the compound of formula III with anisoyl chloride is carried out in the presence of Lewis acid. As Lewis acid, iron(III) chloride or aluminum chloride are applied, in maximum 5 equivalent amount.

The demethylation reaction of the compound of formula VII is carried out in an inert organic solvent or in the mixture of inert organic solvents. As for inert organic solvent, halogenated organic solvents (dichloromethane, dichloroethane, chlorobenzene) are applied.

The demethylation reaction of the compound of formula VII is carried out in the presence of Lewis acid. As for Lewis acid, iron(III) chloride or aluminum chloride is applied.

The demethylation reaction of the compound of formula VII is carried out at a temperature between 20-100° C.

The reaction of the compounds of the formulae V and VI is carried out in an organic solvent or in the mixture of organic solvents. As for organic solvent, alcohols of lower carbon atom number (methanol, ethanol) or ketones of lower carbon atom number (acetone, methyl ethyl ketone) are applied.

The reaction of the compounds of formulae V and VI is performed in the presence of an acid binder of basic character. As for acid binder of basic character, inorganic carbonates are used.

The reaction of the compounds of formulae V and VI is carried out at a temperature around the boiling point of the applied solvent or solvent mixture.

The reaction of the compounds of formulae III and VIII is carried out in an inert organic solvent or in the mixture of inert organic solvents. As for inert organic solvent, halogenated organic solvents (dichloromethane, dichloroethane, chlorobenzene) are applied.

The reaction of the compounds of formulae III and VIII is carried out in the presence of Lewis acid. As for Lewis acid, iron(III) chloride or aluminum chloride is applied.

Preparation of the 2-n-butyl-3-[(di-n-butylamino-3-propoxy)-benzoyl]-5-bis-(methylsulfonamido)-benzofuran of formula II and of the 2-n-butyl-5-bis-(methylsulfonamido)-benzofuran of formula III from 2-n-butyl-5-nitro-benzofuran are known from the literature (EP 0471609 B1, Example 35. and Example 70.

The 2-n-butyl-3-(4-hydroxy-benzoyl)-5-bis-(methylsulfonamido)-benzofuran of formula VI

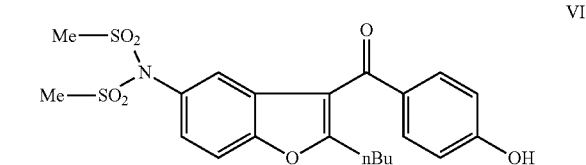

and the 2-n-butyl-5-bis-(methylsulfonamido)-3-(4-methoxy-benzoyl)-benzofuran of formula VII

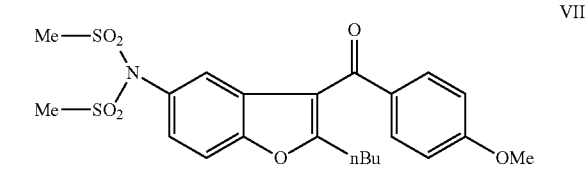

are novel compounds, they are not known from the literature.

The following examples demonstrate further details of the invention—without limiting the claims of the Applicant to the Examples.

EXAMPLE 1

N-[2-n-butyl-3-{4-[(3-di-n-butylamino)-propoxy]-benzoyl}-1-benzofuran-5-yl]-methane-sulfonamide (I)

To 7 g of 2-n-butyl-3-[(di-n-butylamino)-3-propoxy)-4-benzoyl]-5-bis-(methylsulfonamido)-benzofuran (II) the solution prepared from 5 g sodium and 170 ml abs. ethanol is added. The reaction mixture is boiled for 30 minutes, then evaporated under reduced pressure. To the residue 30 ml of dichloromethane and 50 ml of water are added and the mixture is stirred for 20 minutes. The phases are separated. The organic phase is washed with 20 ml of water and evaporated.

Product: oil (yield: 97.9%). Purity (HPLC): 93.1%.

The product is purified through its oxalate salt (yield: 90.3%). Purity (HPLC): 99.5%.

¹H NMR (DMSO): 0.8-0.9 ppm (m, 9H); 1.2-1.5 ppm (m, 10H); 1.67 ppm (5', 2H); 1.87 ppm (5', 2H); 2.38 ppm (t, J=7.2 Hz, 4H); 2.57 ppm (m, 2H); 2.81 ppm (t, J=7.5 Hz, 2H); 2.91 ppm (s, 3H); 4.15 ppm (t, J=6.2 Hz, 2H); 7.09 (d, J=8.8 Hz, 2H); 7.24 ppm (dd, J=8.9; 2.2 Hz, 1H); 7.34 ppm (d, J=2.1 Hz, 1H); 7.65 ppm (d, J=8.8 Hz, 1H); 7.81 ppm (d, J=8.8 Hz, 2H).

EXAMPLE 2

N-[2-n-butyl-3-{4-[(3-di-n-butylamino)-propoxy]-benzoyl}-1-benzofuran-5-yl]-methane-sulfonamide (I)

The process according to Example 1. is performed, with the difference that methanol is used, instead of ethanol.

Yield of the purified product: 88.6%. Purity (HPLC): 99.7%.

EXAMPLE 3

N-[2-n-butyl-3-{4-[(3-di-n-butylamino)-propoxy]-benzoyl}-1-benzofuran-5-yl]-methane-sulfonamide (I)

The process according to Example 1. is performed, with the difference that potassium is used instead of sodium.

Yield of the purified product: 88.9%. Purity (HPLC): 99.5%.

EXAMPLE 4

N-[2-n-butyl-3-{4-[(3-di-n-butylamino)-propoxy]-benzoyl}-1-benzofuran-5-yl]-methane-sulfonamide (I)

To 22 g of the unpurified dronedarone (I) which contains 4% of the bis-methanesulfonamido compound (II), 0.8 g of sodium metal dissolved in 220 ml of abs. ethanol is added. The reaction mixture is boiled for 30 minutes, then evaporated. To the residue 140 ml of water and 80 ml of dichloromethane are added and the reaction mixture is stirred for 20 minutes. The phases are separated, the dichloromethane phase is evaporated. The crude dronedarone (I) is purified through its oxalate salt.

Yield of the purified product: 93.5%. Purity (HPLC): 99.4%.

EXAMPLE 5

2-n-butyl-5-bis-(methylsulfonamido)-3-(4-methoxy-benzoyl)-benzofuran (VII)

4 g of 2-n-butyl-5-bis-(methylsulfonamido)-benzofuran (III) and 2.29 g of anisoyl chloride are dissolved under stirring in 20 ml of dichloromethane. The solution is cooled to 5-10° C. and at this temperature 2.16 g of iron(III) chloride is added in four portions, in a period of 15 minutes. The mixture is heated to 20° C. and stirred at that temperature for 1 hour. The reaction mixture is then heated to 40° C. and at this temperature 30 ml of water is added to it in 30 minutes. The phases are separated at this temperature. The dichloromethane phase is washed with 10 ml of water, 2×10 ml of 5% aqueous sodium hydrogen carbonate solution and 2×10 ml of water. The dichloromethane phase is evaporated.

Product: oil (yield: 95.98%). Purity (HPLC): 99.0%.

¹H NMR (DMSO-d6): 7.86 ppm (d, J=8.6 Hz, 2H); 7.80 ppm (d, J=8.7 Hz, 1H); 7.55 ppm (d, J=1.9 Hz, 1H); 7.51 ppm (dd, J=8.7 Hz, 2.0 Hz, 1H); 7.12 ppm (d, J=8.7 Hz, 2H); 3.9 ppm (s, 3H); 3.53 ppm (s, 6H); 2.84 ppm (t, J=7.4 Hz, 2H); 1.7 ppm (5', J=7.3 Hz, 2H); 1.27 ppm (6', J=7.4 Hz, 2H); 083 ppm (t, J=7.4 Hz, 3H).

Molecular mass: [M+H]⁺ calculated: 480.1151 Da; [M+H]⁺ measured: 480.1142 Da.

EXAMPLE 6

2-n-butyl-3-(4-hydroxy-benzoyl)-5-bis-(methylsulfonamido)-benzofuran (VI)

5.3 g of 2-n-butyl-5-bis-(methylsulfonamido)-3-(4-methoxy-benzoyl)-benzofuran (VII) is dissolved in 12 ml of chlorobenzene. The solution is then added at 64-66° C. to the suspension made of 4.44 g of aluminum chloride and 17 ml of chlorobenzene, so that half of the amount of the solution is added in 30 minutes and the other half in 3 hours. After the addition the mixture is stirred at 64-66° C. for 4 hours and at that temperature 25 ml of water is added in 10 minutes. The phases are still hot separated. The chlorobenzene phase is stirred at 65° C. with 3×25 ml of water, the phases are separated and the organic phase is evaporated.

Product: oil (yield: 94.0%). Purity (HPLC) 99.0%.

¹H NMR (DMSO): 0.84 ppm (t, J=7.4 Hz, 3H); 1.27 ppm (6', J=7.3 Hz, 2H); 1.70 ppm (5', J=7.4 Hz, 2H); 2.85 ppm (t, J=7.3 Hz, 2H); 3.53 ppm (s, 6H); 6.93 ppm (s, J=8.5 Hz, 2H); 7.50 ppm (dd, J=8.6 Hz, 1.8 Hz, 1H); 7.54 ppm (d, J=1.9 Hz, 1H); 7.77 ppm (d, J=8.5 Hz, 2H); 7.79 ppm (d, J=8.7 Hz, 1H); 10.54 ppm (s, 1H)

Molecular mass: [M+H]⁺ calculated: 466.0994 Da; [M+H]⁺ measured: 466.1001 Da.

EXAMPLE 7

2-n-butyl-3-(4-hydroxy-benzoyl)-5-bis-(methylsulfonamido)-benzofuran (VI)

The process according to Example 6 is performed with the difference that dichloroethane is used as solvent.

Yield of the product: 97.0%. Purity (HPLC): 99.1%.

EXAMPLE 8

2-n-butyl-3-[(di-n-butylamino-3-propoxy)-4-benzoyl]-5-bis-(methylsulfonamido)-benzofuran (II)

2 g of 2-n-butyl-3-(4-hydroxy-benzoyl)-5-bis-(methylsulfonamido)-benzofuran (V) and 0.88 g of (3-di-n-butylamino)-propyl chloride are dissolved in 16 ml of methyl ethyl ketone. 1.75 g of potassium carbonate is added to the solution and the reaction mixture is boiled for 8 hours. The inorganic salts are filtered off, washed with 16 ml of methyl ethyl ketone. The solvent is removed by evaporation.

Product: oil (2.56 g, yield: 93.5%) Purity (HPLC): 99.1%

¹H NMR (DMSO-d6): 7.87 ppm (d, J=8.8 Hz, 2H); 7.81 ppm (d, J=8.8 Hz, 1H); 7.53 ppm (d, J=2.3 Hz, 1H); 7.52 ppm (dd, J=8.8; 2.3 Hz, 1H); 7.12 ppm (d, J=8.8 Hz, 2H); 4.21 pp (w, 2H); 3.53 ppm (s, 6H); 3.26 ppm (w, 2H); 3.03 ppm (w, 4H); 2.84 ppm (t, J=7.5 Hz, 2H); 2.19 ppm (w, 2H); 1.70 ppm (5', J=7.4 Hz, 2H); 1.68 ppm (w, 4H); 1.36 ppm (6', J=7.0 Hz, 4H); 1.27 ppm (6', J=7.3 Hz, 2H); 0.94 ppm (t, J=7.2 Hz, 6H); 0.84 ppm (t, J=7.4 Hz, 3H)

EXAMPLE 9

2-n-butyl-3-[(di-n-butylamino-3-propoxy)-4-benzoyl]-5-bis-(methylsulfonamido)-benzofuran (II)

2 g of 2-n-butyl-5-bis-(methylsulfonamido)-benzofuran (III) is dissolved in 10 ml of dichloromethane and to the solution 1.8 g of the hydrochloride of 4-(di-n-butylaminopropoxy)benzoyl chloride (VIII) is added. The mixture is cooled to 5° C. and in four portions, in 15 minutes 0.93 g of iron(III) chloride is added. The reaction mixture is heated to 20° C. and stirred at that temperature for 1 hour, then heated to 35-40° C. and 16 ml of water is added to it. After stirring for 30 minutes the phases are separated. The dichloromethane phase is washed at 35-40° C. with 6 ml of water, 2×6 ml of 5% aqueous sodium hydrogen carbonate solution and 2×60 ml of water. The dichloromethane is removed by evaporation.

Product: oil (3.5 g yield: 95.2%). Purity: (HPLC) 89.2%

The product is identical with the compound prepared in Example 8.

What is claimed is:

1. A process for the preparation of N-[2-n-butyl-3-{4-[(3-dibutylamino)-propoxy]-benzoyl}-1-benzofuran-5-yl]-methane-sulfonamide of formula I:

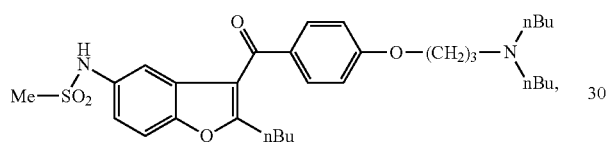

or a pharmaceutically acceptable salt thereof,
comprising selectively cleaving in the presence of alkali alcoholate, one of the methylsulfonyl groups of the 2-n-butyl-3-[(di-n-butylamino-3-propoxy)-benzoyl]-5-bis-(methylsulfonamido)-benzofuran of formula II:

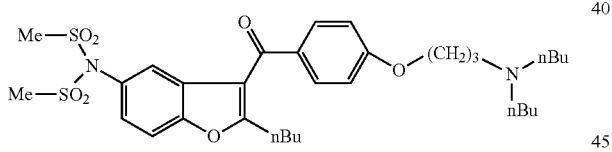

and if desired, transforming the resulting compound of formula I into its salt.

2. The process as defined in claim 1, further comprising carrying out the selective cleavage in an organic solvent or in a mixture of organic solvents.

3. The process as defined in claim 1, comprising
a) reacting the 2-n-butyl-5-bis-(methylsulfonamido)-benzofuran of formula III:

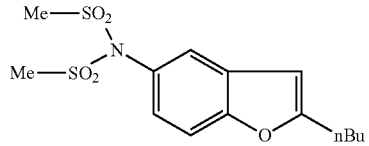

with anisoyl chloride in the presence of a Lewis acid, and
b) demethylating the resulting 2-n-butyl-5-bis-(methylsulfonamido)-3-(4-methoxy-benzoyl)-benzofuran of formula VII:

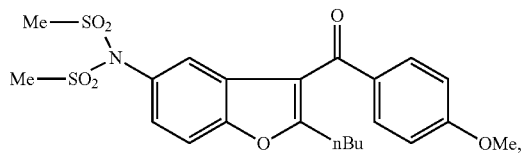

and
c) reacting the resulting 2-n-butyl-3-(4-hydroxy-benzoyl)-5-bis-(methylsulfonamido)-benzofuran of formula VI:

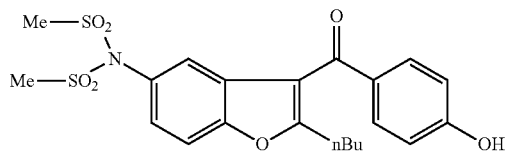

with 3-(di-n-butyl-amino)-propyl-chloride of formula V:

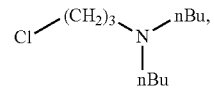

and
d) selectively cleaving one of the methylsulfonyl groups of the resulting 2-n-butyl-3-[(di-n-butylamino-3-propoxy)-benzoyl]-5-bis-(methylsulfonamido)-benzofuran of formula II:

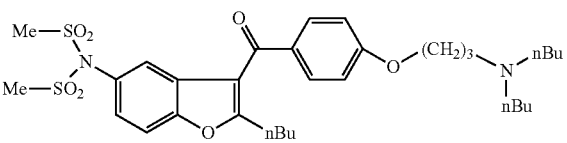

and if desired, transforming the thus obtained compound of formula I into its salt.

4. The process according to claim 3, comprising performing reaction step b) in the presence of a Lewis acid.

5. The process according to claim 3, comprising carrying out reaction step b) in an inert organic solvent or in a mixture of inert organic solvents.

6. The process according to claim 3, comprising carrying out reaction step b) at a temperature between 20-100° C.

7. The process according to claim 3, comprising carrying out reaction step c) at the boiling point of the applied solvent or solvent mixture.

8. The process according to claim 3, comprising carrying out reaction step c) in an inert organic solvent or in a mixture of inert organic solvents.

9. The process according to claim 3, comprising carrying out reaction step c) in the presence of an acid binder of basic character.

10. The process according to claim 1, comprising
a) reacting the 2-n-butyl-5-bis-(methylsulfonamido)-benzofuran of formula III:

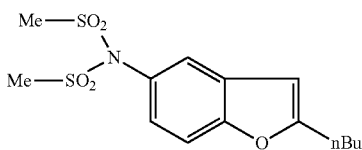

in the presence of a Lewis acid with the hydrochloride of the 4-(3-di-n-butylamino-propoxy)-benzoyl chloride of formula VIII:

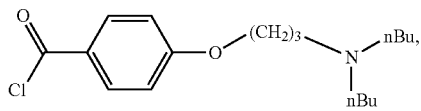

and b) selectively cleaving one of the methylsulfonyl groups from the resulting 2-n-butyl-3-[(di-n-butylamino-3-propoxy)-benzoyl]-5-bis-(methylsulfonamido)-benzofuran of formula II:

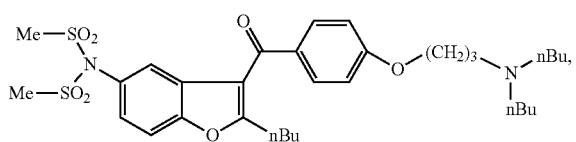

and if desired, transforming the thus obtained compound of formula I into its salt.

11. The process according to claim 3, comprising using iron(III) chloride or aluminium(III) chloride in reaction step a) as the Lewis acid.

12. The process according to claim 4, comprising using iron(III) chloride or aluminium(III) chloride in reaction step a) as the Lewis acid.

13. The process according to claim 10, comprising using iron(III) chloride or aluminium(III) chloride in reaction step a) as the Lewis acid.

14. The process according to claim 3, comprising carrying out reaction step a) in an inert organic solvent or in a mixture of inert organic solvents.

15. The process according to claim 11, comprising carrying out reaction step a) in an inert organic solvent or in the mixture of inert organic solvents.

16. The compound 2-n-butyl-3-(4-hydroxy-benzoyl)-5-bis-(methylsulfonamido)-benzofuran of formula VI:

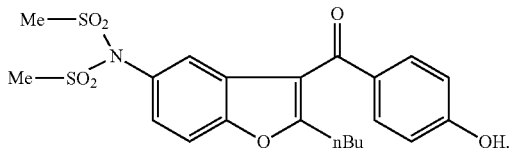

17. The compound 2-n-butyl-5-bis-(methylsulfonamido)-3-(4-methoxy-benzoyl)-benzofuran of formula VII:

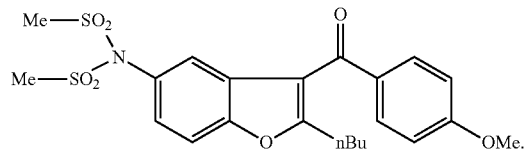

* * * * *